(12) United States Patent
Niehren

(10) Patent No.: US 8,945,866 B2
(45) Date of Patent: *Feb. 3, 2015

(54) METHOD AND APPARATUS FOR CUTTING AND COLLECTING DISSECTED SPECIMENS

(75) Inventor: Stefan Niehren, Altomuenster (DE)

(73) Assignee: Molecular Machines and Industries AG, Glattbrugg (CH)

( * ) Notice: Subject to any disclaimer, the term of this patent is extended or adjusted under 35 U.S.C. 154(b) by 1008 days.

This patent is subject to a terminal disclaimer.

(21) Appl. No.: 11/837,006

(22) Filed: Aug. 10, 2007

(65) Prior Publication Data

US 2008/0064077 A1 Mar. 13, 2008

(30) Foreign Application Priority Data

Aug. 11, 2006 (EP) .................................. 06016816

(51) Int. Cl.
*G01N 1/30* (2006.01)
*G01N 33/48* (2006.01)
*G01N 1/00* (2006.01)
*G01N 1/28* (2006.01)
*G02B 21/32* (2006.01)

(52) U.S. Cl.
CPC .............. *G01N 1/2813* (2013.01); *G02B 21/32* (2013.01); *G01N 2001/282* (2013.01); *G01N 2001/284* (2013.01)
USPC ........................... 435/40.5; 435/40.51; 356/36

(58) Field of Classification Search
CPC ................. C12Q 2565/601; B01L 2400/0454; G01N 1/28; G01N 2001/045; G01N 2001/2833; G01N 2001/2886; G01N 2035/00237
USPC ....................................................... 435/40.5
See application file for complete search history.

(56) References Cited

U.S. PATENT DOCUMENTS

| 5,998,129 A | 12/1999 | Schutze et al. |
| 6,100,051 A | 8/2000 | Goldstein |
| 2006/0087643 A1 | 4/2006 | Donovan |
| 2006/0139621 A1 | 6/2006 | Baer |

FOREIGN PATENT DOCUMENTS

| DE | 201 00 866 | 4/2001 |
| WO | 9835216 | 8/1998 |
| WO | 9900658 | 1/1999 |
| WO | 0133190 | 5/2001 |

*Primary Examiner* — Sharmila G. Landau
*Assistant Examiner* — Sheridan Macauley
(74) *Attorney, Agent, or Firm* — Pabst Patent Group LLP

(57) ABSTRACT

Methods and devices for cutting and collecting dissected specimens are described herein. In one embodiment, the method for dissecting and collecting specimens includes the following steps: placing a sample onto a slide of a laser dissection microscope, the slide being translatable in its plane of extension, lowering an adherent collection device centered on the optical axis onto the probe, wherein the adherent collection device, in its lowered state, adheres to the sample, is freely translatable with the slide and decoupled from the optical axis of the microscope, and, in its raised state, is fixed relative to the optical axis, dissecting one or more specimens from the sample, wherein the following steps are performed if the next specimen to be dissected is located outside of a predetermined collection radius of the adherent collection device: raising the adherent collection device, translating the slide to a given position relative to the optical axis of the microscope in order to decenter the center of the specimen to be dissected from the optical axis of the microscope, lowering the adherent collection device onto the sample, and dissecting one or more subsequent specimens, wherein, after each step of raising the adherent collection device, the predetermined position is spaced apart from all previously determined positions by at least one predetermined distance.

10 Claims, 7 Drawing Sheets

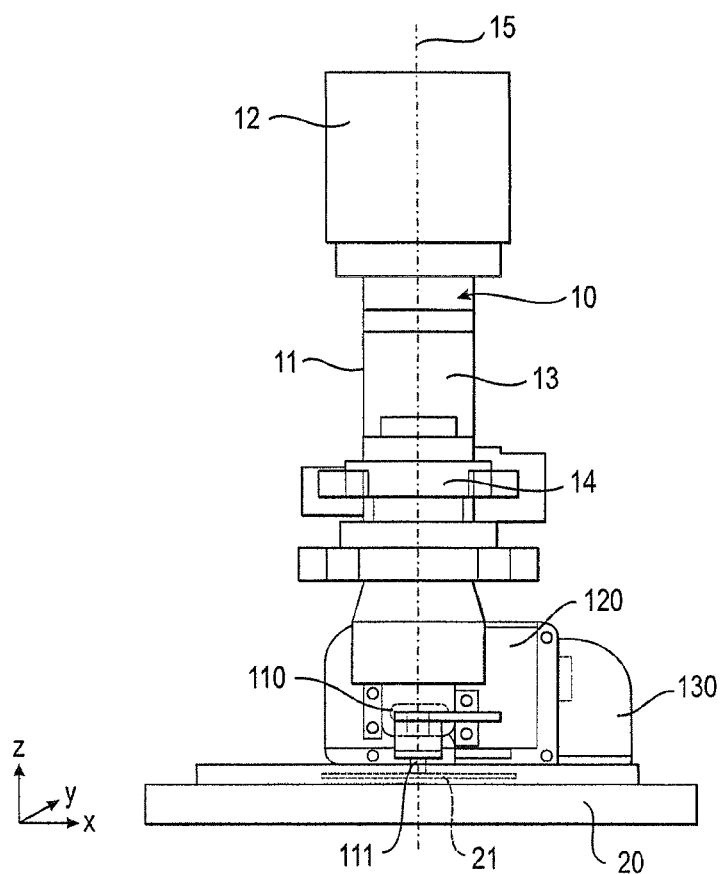

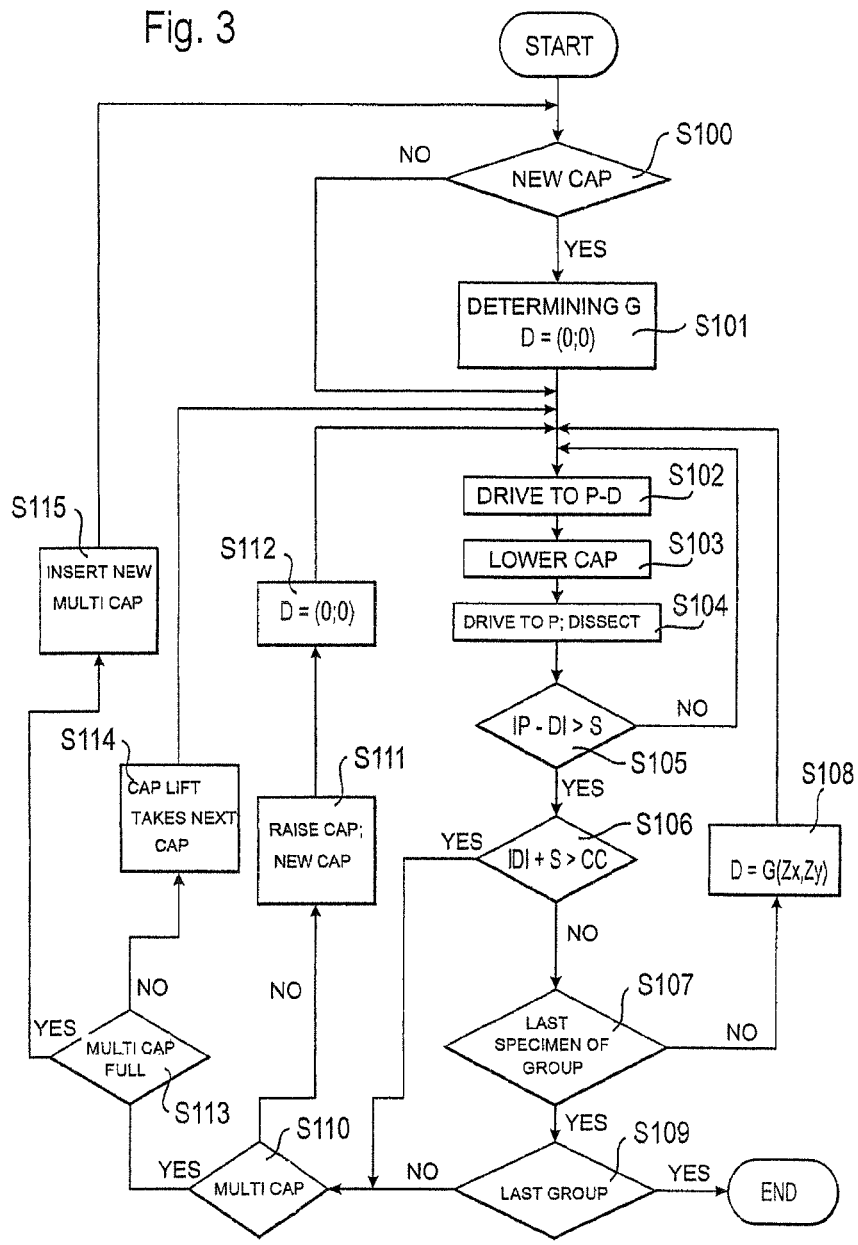

METHOD AND APPARATUS FOR CUTTING AND COLLECTING DISSECTED SPECIMENS

CROSS-REFERENCE TO RELATED APPLICATION

This application claims priority under 35 U.S.C. §119 to EP application 06016816.8 filed Aug. 11, 2006 and where permissible is incorporated by reference in its entirety.

TECHNICAL FIELD

The present invention relates to a method for cutting and collecting dissected specimens from samples, as well as to a laser dissection microscope suitable for performing this method.

BACKGROUND OF THE INVENTION

In laser microdissection, in particular of biological or medical samples such as tissue biopsy samples, a sample having a thickness of generally 5 to 10 micrometers is placed upon a slide of a laser dissection microscope, whereafter dissected specimens are cut from the sample by means of a finely focused laser beam of an infrared (IR) laser diode (for example AlGaAs laser diode). To that end, a transparent thermoplastic transfer film selectively absorbing in the infrared emission spectrum of the laser diode is placed over the sample. The film is melted at well defined locations and adheres to the desired part of the sample to be cut (dissected specimen). The dissected specimen may comprise single cells or a group of cells, for example, which need to be extracted from the probe for further analysis. In other words, the dissected specimens, the size of which is of the order of about 1 to 10 micrometers, need to be collected after cutting. Here, several problems arise, in particular if a plurality of dissected specimens has to be cut and collected. The sample is, moreover, thermally affected since the IR laser beam employed for cutting transfers heat onto the sample and may, thereby, damage the sample such as, in this example, the cells.

Several methods are known in the art for collecting dissected specimens German Patent No. DE 20100866 U describes, for example, a carrier device which freely supports the transfer film with the sample within the frame and from which the film with the dissected specimen falls down into a receptacle after having been cut by the laser beam. This method has, however, the following disadvantages. On the one hand there is the lack of referenceability of the dissected specimens because all dissected specimens fall into the receptacle in an uncontrolled manner and thus cannot be related to their original positions. Further, due to their merely gravity-induced free fall, small dissected specimens, in particular, may be lost for analysis if they get caught on parts of the microscope or the walls of the receptacle their electrostatic interactions.

U.S. Pat. No. 5,998,129 describes a laser microdissection method, wherein a desired region, for instance cellular organelles or single cells, is cut out from the surrounding tissue of a tissue sample placed upon a planar slide by means of a laser beam. The isolated cell, which is still present on the slide, is catapulted along the laser beam by an additional laser pulse and caught in a reaction receptacle. Due to the transfer of momentum from the laser beam the dissected specimens again fly into the reaction receptacle in an uncontrolled manner and can no longer be referenced. Additionally, large dissected specimens cannot be catapulted and have to be separated beforehand.

A further known method comprises the use of an adherent collection device, a so-called cap. First, several dissected specimens are cut from the sample, then the cap is lowered onto the sample and the dissected specimens are adhered to the cap. The cap with the adhered dissected specimens is raised within the microscope and removed. Although in this method the cap can take up several dissected specimens and is thus capable of working faster, the problem arises that due to the different sizes and shapes of the dissected specimens, the limited reception area and adherability of the cap and the possible inclination of the cap upon adhering the cap surface is used only insufficiently leading to an inevitable waste of the expensive caps. If, on the other hand, several dissected specimens are stacked upon another, the danger arises that the dissected specimens may fall down in an uncontrolled way and be lost. Thus, the number of samples on the cap is severely limited, which is a disadvantage since in some applications the number of dissected specimens may then not be sufficient for analysis.

It is therefore an object of the present invention to provide a method and an apparatus solving the above-mentioned problems and allowing a contamination-free, secure, efficient and cost effective collection of dissected specimens of different sizes without damaging the samples or presenting a complicated design or structure.

SUMMARY OF THE INVENTION

Methods and devices for cutting and collecting dissected specimens are described herein. In one embodiment, the method includes the following steps: placing a biological sample onto a slide of a laser dissection microscope, the slide being translatable in its plane of extension; lowering an adherent collection device centered on the optical axis onto the biological sample, wherein the adherent collection device, in its lowered state, adheres to the sample, is freely translatable with the slide, and is decoupled from the optical axis of the microscope and, in its raised state, is fixed relative to the optical axis; cutting one or more specimens from the biological sample, wherein the following steps are performed if the next specimen to be cut is located outside of a predetermined collection radius of the adherent collection device: raising the adherent collection device; translating the slide to a predetermined position relative to the optical axis of the microscope in order to decenter the center of the next specimen to be cut from the optical axis of the microscope; lowering the adherent collection device onto the biological sample; and cutting one or more subsequent specimens, wherein after each step of raising the adherent collection device the predetermined position is spaced apart from all previously determined positions by at least a predetermined distance.

In another embodiment, the method includes the following steps: placing a biological sample onto a slide of a laser dissection microscope, the slide being translatable in its plane of extension, cutting the specimens from the biological sample and collecting the dissected specimens by lowering a adherent collection device centered on the optical axis onto the biological sample, wherein the adherent collection device, in its lowered state, adheres to the sample, is freely translatable with the slides, and in its raised state is decoupled from the optical axis of the microscope and is fixed relative to the optical axis, wherein the following steps are performed if a next specimen to be collected is located outside of a predetermined collection radius of the adherent collection device: raising the adherent collection device, translating the slide to a given position relative to the optical axis of the microscope in order to decenter the center of the subsequent specimen to be collected from the optical axis of the microscope, lowering the adherent collection device onto the biological sample, and adhering one or more subsequent dissected specimens to the adherent collection device, wherein after each step of raising the adherent collection device the predetermined position is spaced apart from all previously determined positions by at least a predetermined distance.

A laser dissection microscope may be used to perform these methods. In a preferred embodiment, the laser dissection microscope contains a slide for receiving a biological sample, wherein the slide is freely translatable in its plane of extension, an adherent collection device capable of being lowered onto and raised from the biological sample on the slide, the adherent collection device, in its lowered state, being freely translatable with the slide and decoupled from the optical axis of the microscope and, its raised state, being fixed relative to the optical axis in.

BRIEF DESCRIPTION OF THE DRAWINGS

FIG. 1b shows a front view of the microscope of FIG. 1a.
FIG. 2a shows a partial cross-section from above of a cap lift module of the microscope of FIG. 1a.
FIG. 2b shows a partial lateral cross-section of the cap lift module of FIG. 2a.
FIG. 2c shows a partial front cross-section view of the cap lift module of FIG. 2a.
FIG. 3 shows a flow chart illustrating an embodiment of the method for cutting and collecting dissected specimens.

DETAILED DESCRIPTION OF THE INVENTION

Figure 1A:
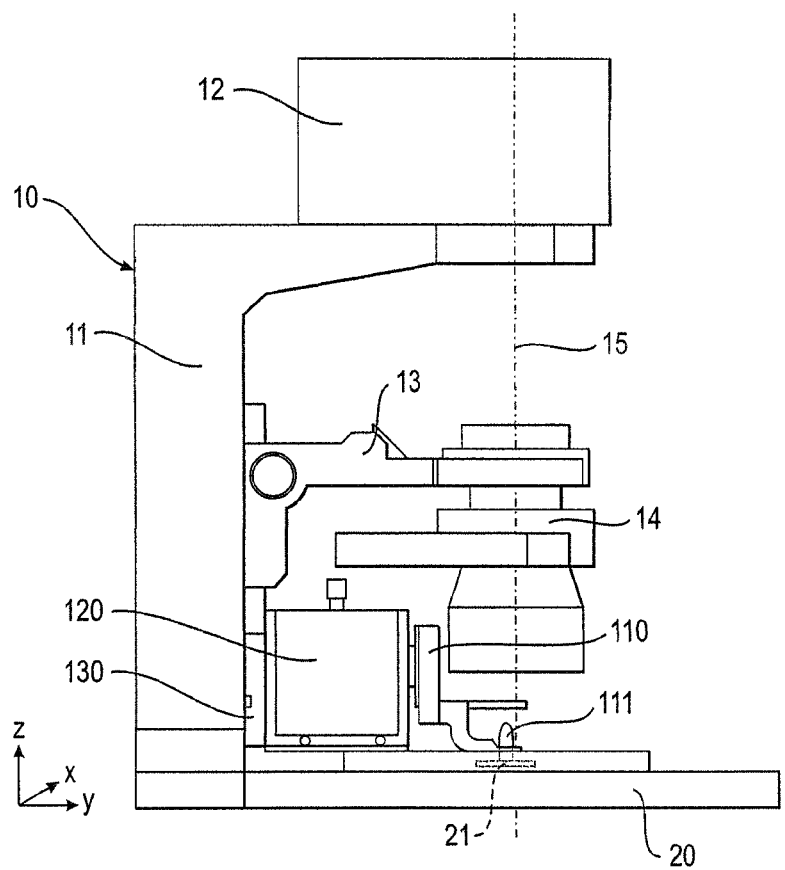
FIG. 1a shows a side view of a laser dissection microscope.

Methods and devices for cutting and collecting dissected specimens are described herein. In one embodiment, the method includes the following steps: placing a biological sample onto a slide of a laser dissection microscope, the slide being translatable in its plane of extension; lowering an adherent collection device centered on the optical axis onto the biological sample, wherein the adherent collection device, in its lowered state, adheres to the sample, is freely translatable with the slide, and is decoupled from the optical axis of the microscope and, in its raised state, is fixed relative to the optical axis; cutting one or more specimens from the biological sample, wherein the following steps are performed if the next specimen to be cut is located outside of a predetermined collection radius of the adherent collection device: raising the adherent collection device; translating the slide to a predetermined position relative to the optical axis of the microscope in order to decenter the center of the next specimen to be cut from the optical axis of the microscope; lowering the adherent collection device onto the biological sample; and cutting one or more subsequent specimens, wherein after each step of raising the adherent collection device the predetermined position is spaced apart from all previously determined positions by at least a predetermined distance.

Alternatively, the method for cutting and collecting dissected specimens includes the following steps: placing a biological sample onto a slide of a laser dissection microscope, the slide being translatable in its plane of extension, cutting the specimens from the biological sample and collecting the dissected specimens by lowering a adherent collection device centered on the optical axis onto the biological sample, wherein the adherent collection device, in its lowered state, adheres to the sample, is freely translatable with the slides, and in its raised state is decoupled from the optical axis of the microscope and is fixed relative to the optical axis, wherein the following steps are performed if a next specimen to be collected is located outside of a predetermined collection radius of the adherent collection device: raising the adherent collection device, translating the slide to a given position relative to the optical axis of the microscope in order to decenter the center of the subsequent specimen to be collected from the optical axis of the microscope, lowering the adherent collection device onto the biological sample, and adhering one or more subsequent dissected specimens to the adherent collection device, wherein after each step of raising the adherent collection device the predetermined position is spaced apart from all previously determined positions by at least a predetermined distance.

Both methods make it possible to efficiently utilize the entire adherent surface ("KF") of the adherent collection device, to avoid a stacking of dissected specimens and to increase the overall collection efficiency. Moreover, with both methods the above-mentioned disadvantages of the known methods such as the thermal stress applied to the probe and the uncontrolled flying or falling of the dissected specimens are avoided.

In a preferred embodiment of the method, the predetermined distance is defined by the size of the dissected specimens. Since the dissected specimens mostly have different sizes, the predetermined distance may be defined by the mean size, for example, of the specimens to be cut. The maximum size may be used as well. The method thus allows all sizes of samples to be cut.

In a preferred embodiment of the method, the positions are located one after another along a spiral path. This facilitates an unequivocal identification of the dissected specimens and allows a high density of dissected specimens on the adherent collection device.

In its lowered state, the adherent collection device preferably lies flat upon the biological sample. This improves the adherence of the dissected specimen to the adherent collection device, provides a larger adherent surface and allows thus a larger collection capacity. It is preferred that the adherent collection device, in its lowered state, lies on the biological sample with a controlled contact pressure. Thereby the collection performance can be increased while at the same time damage to the sample or the dissected specimen can be avoided. Moreover, the planarity of the sample is not disturbed so that the sample remains in the imaging plane of the microscope and the cutting plane of the laser.

In a further preferred embodiment, after the step of placing the sample onto the slide, the specimen(s) to be dissected is/are predetermined and, after any one step of raising the adherent collection device, the slide is translated relative to the adherent collection device so that the adherent collection device is located above a sample-free portion of the slide, followed by a step of determining the number and/or area of the dissected specimens and by a step of comparing the determined size and/or area with the number and area of the predetermined specimens before dissection. By means of this sample inspection, the user may determine if the sample specimens predetermined by him have actually been dissected (cut) and collected. This is particularly important for small specimens or with a large number of specimens. In this context, "predetermined" means that at least one of the specimens' number, shape, size, area, position or the like are determined or set in advance, for example by means of a computer-based graphical method.

Preferably, the step of predetermining comprises a step of setting a limit value for the difference in number and/or area between predetermined and determined numbers and/or areas of the specimens to be dissected. The step of setting a limit value is particularly important in the analysis of DNA, RNA and proteins as well as in the field of forensics since the quantity of specimens actually dissected and, thus, available for subsequent analysis may have a decisive impact upon the analysis result.

It is further preferred to perform the step of comparing by means of image analysis software. Employing image analysis software allows complete automation of the sample inspection and increases the reliability and process safety of the dissection process.

According to another preferred embodiment, after the step of comparing, the adhesive collection device is translated back above the sample in order to dissect (cut) specimens that have not been dissected or adhered to the adhesive collection device properly, in accordance with the results of the comparison.

Moreover, it is advantageous to perform, after the step of comparing, a step of removing from the adhesive collection device any undesired sample material by means of laser ablation. This results in a further increase in process accuracy and reliability.

It is to be understood that the above-mentioned sample inspection method may be applied to other dissection methods, including other laser dissection methods, in which biological samples need to be dissected and collected.

A laser dissection microscope for cutting and collecting dissected specimens contains a slide for receiving a biological sample, wherein the slide is freely translatable in its plane of extension, an adherent collection device capable of being lowered onto and raised from the biological sample on the slide, the adherent collection device, in its lowered state, being freely translatable with the slide and decoupled from the optical axis of the microscope and, its raised state, being fixed relative to the optical axis in.

Due to the free translatability in its lowered state, it is possible for the microscope to position the adherent collection device relative to the slide with the sample in a concerted and controlled way and, thus, to efficiently utilize the adherent collection device.

Preferably, the laser dissection microscope further comprises a magnet for controlling the contact pressure of the adherent collection device. An especially fine adjustment of the contact pressure may thus be realized.

In a particularly advantageous embodiment, the magnet is freely tuneable so that the relative distance between the adherent collection device and the sample can be adjusted. The collected dissected specimens on the cap may thus be lowered, for example during process control, to just above the sample and be visually observed without adhering to the sample.

Advantageously, in the laser dissection microscope, the distance between the adherent collection device and the sample is adjustable. Thus it is possible to lower the adherent collection device, for example for purposes of process control, to just above the sample without touching it. The adherent collection device can then be observed with the microscope while being virtually in focus, without any contact with the sample affecting the observation.

It is further preferred that the laser dissection microscope comprises several adherent collection devices or one or more arrays of adherent collection devices. Thereby, several groups of dissected specimens may be processed in sequence without any user intervention for changing the adherent collection device interrupting the dissection.

FIGS. 1a and 1b show a laser microdissection microscope according to one embodiment described herein. The laser microdissection microscope contains a microscope illuminating unit 10 consisting of an illumination arm 11, a lamp housing 12 having a filter and a lamp, and a condenser support 13 attached to the illumination arm and having condenser lens 14. In the lower part of the microscope there is a table 20 translatable in the XY plane, to which the slide 21 with the sample 22 is secured. The optical axis of the microscope is shown as a dash-dotted line and indicated by reference numeral 15.

Under the condenser support 13 there is the cap lift module comprising as essential elements the cap lift 120, the cap lift arm 110 and the actual cap 111 (adherent collection device) The cap lift 120 is attached to the illumination arm 11 of the microscope through the cap lift holder 130.

Figure 2A:
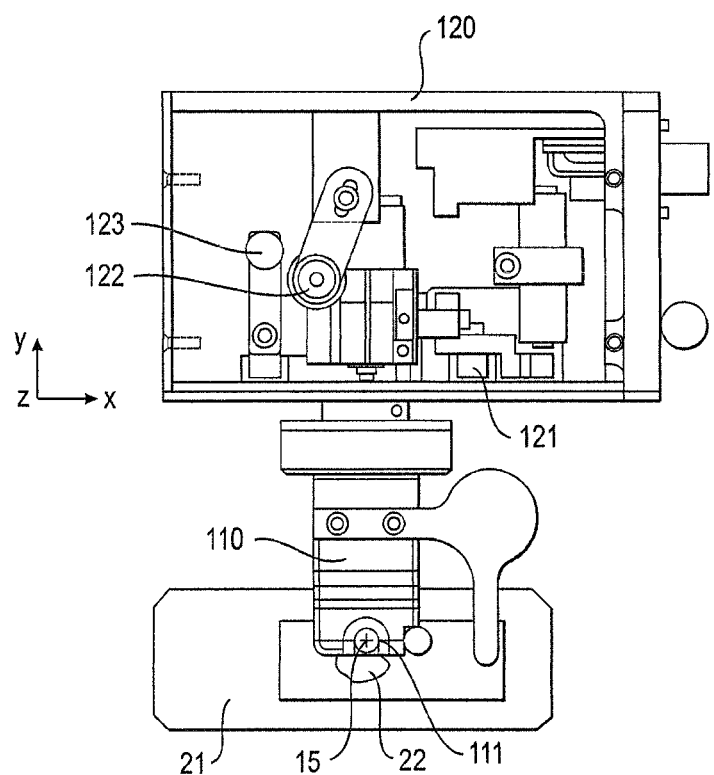
Figure 2B:
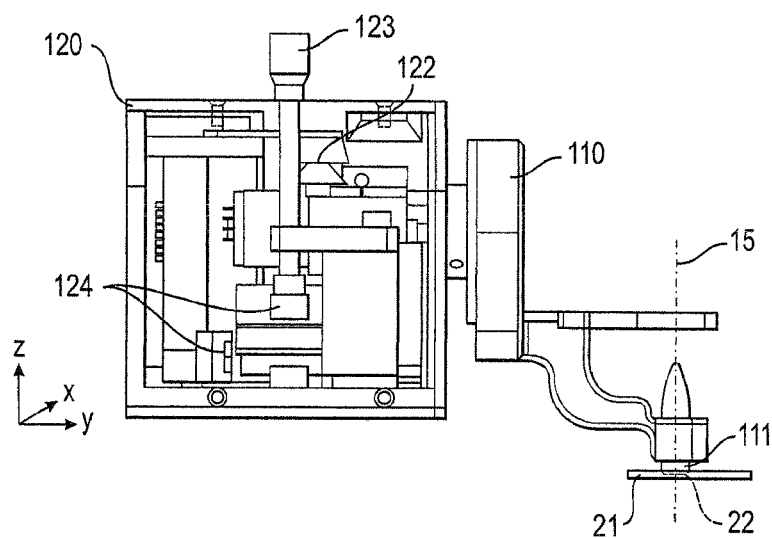
Figure 2C:
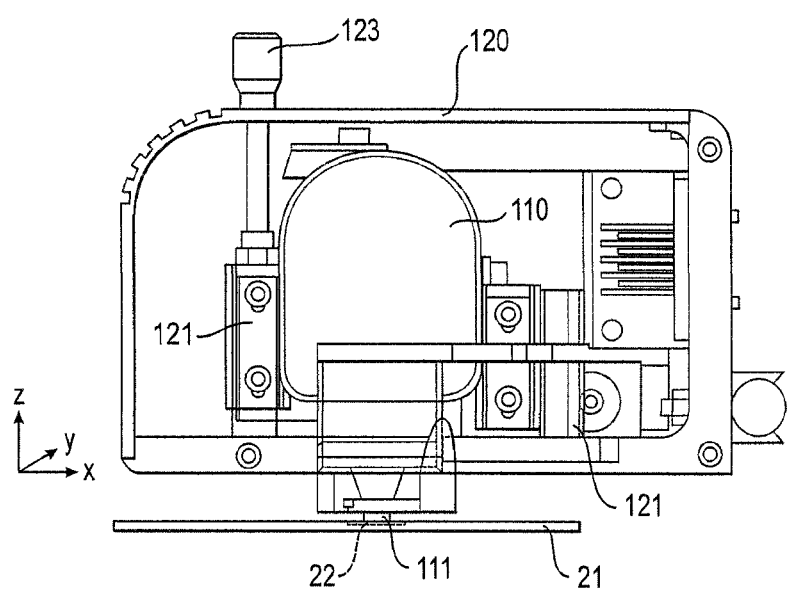

FIGS. 2a, 2b and 2c show in detail the structure of the cap lift module. Within the cap lift 120 there is a height adjustment 121, by which the cap lift arm 110 may be adjusted in its height relative to the XY table 20. Reference numeral 122 indicates an adjustment mechanism for centering the cap onto the optical axis 15 of the microscope, and reference numeral 123 indicates a control device of the contact pressure of the cap onto the sample, which adjusts the position of the magnet 124.

The cap lift arm 110 may occupy at least two different positions, on the one hand a raised upper position and on the other hand a bottom lowered position, as well as one or more floating positions, in which the cap does not touch the sample. In the upper position the cap lift arm 110 is fixed relative to the optical axis 15 of the microscope, while in the lower position and in the floating positions it is decoupled from the optical axis. In this position, the cap lift arm 110 is freely movable in the X and Y directions. This is necessary so that the cap lift arm 110 with the cap 111 may move together with the XY table 120 during cutting and translation. The adjustable tolerance (maximum excursion) ("FR") is up to +/− 10 mm. Within this tolerance the cap 111 always lies flat upon the sample 22 or floats parallel above it. If the adjusted tolerance is exceeded, a controller (not shown) may automatically raise the cap 111.

In the following, an embodiment of the methods disclosed herein is illustrated in the flow chart of FIG. 3.

First, at the start of the method (S100) it is checked if a new unused cap is employed, and if the answer is yes, center positions and intersection lines of one or more groups of specimens to be cut are input into the controller. The controller also knows further parameters, such as the collection radius S of the cap. Within a collection radius as defined by the user, all samples are cut without raising the cap. If further specimens to be dissected are on the sample, but are located outside of the collection radius S, the cap lift has to be raised and repositioned.

A virtual grid having a grid width G is now superimposed on the cap (S101). The grid constant G is set in accordance with the mean size of the objects to be cut (specimens) in the respective group and is defined as a multiple Q, chosen by the user, of the sum of the mean diameter $d_{ave}$ of the specimens defined in the group and twice the various of the diameters, $\sigma_d$:

$$G = Q \cdot (d_{ave} + 2\sigma_d).$$

With a yet unused cap, to which no specimens are yet adhered, the raised cap 111 is centered onto the optical axis 15 of the microscope, that is the distance D=(0; 0) is set and the grid cell (0,0) is used. In other words, the first dissected specimen is adhered in the center of the cap. The slide is now translated according to the intersection lines and the center positions to the specimen positions P (S102 with D=(0; 0).

If a position P is, however, situated outside the collection radius S, the cap has to be repositioned. In this case the (next) object to be cut is moved to a new grid cell position P−D (S102). The center of the dissected specimen now no longer lies on the optical axis 15 but is spaced apart from it by a distance D=(Dx; Dy). The distance D (grid shift) may be determined in several ways, one of which is illustrated below. The condition is that the dissected specimen does not encounter a specimen already present on the cap 111, that is that the new position is separated from the old one by the grid constant. The cap shift D is calculated according to the cell indices (Zx; Zy), $$D=(G \cdot Zx;\ G \cdot Zy).$$

The cap 111 is then lowered to the lower position (S103). Only now the center of the dissected specimen is translated into the optical axis 15 (laser) by moving the XY table 20, and the next object is cut with the cap lying thereon (S104). Thus, the cap is moved away from the center of the dissected specimens by the controlled distance D.

If the next specimen to be dissected lies outside the collection radius of the cap, that is if |P−D|>S (S105), then—if the cap is not yet full—|D|+S>CC (S106), and if the last specimen of the group is not yet dissected (S107), the cap is raised and the next grid cell is used (S108). The parameter CC corresponds to the capacity of the cap. This cap capacity ("CC") is a measure for the maximum useful area of the cap and is determined by the minimum of the tolerance FR of the cap and the usable adherent surface KF of the cap (CC=min (FR, KF)). In other words, if the cap has to be translated by more than the useful cap capacity in order to realize the grid shift, it is assumed that the cap is full (see S106). In this case, the cap has to be raised, and a new cap has to be attached to the cap lift arm 110 (S111). The new cap is then centered again onto the optical axis (S112).

In a further embodiment, which is also contemplated in the flow chart of FIG. 3, several groups of specimens are dissected. Here, so called "multi cap systems" may be utilized, which consist of several caps held simultaneously on the cap lift arm 110. If the cap in actual use is full (S106) or the last specimen of the group is dissected (S107) and the last group is not yet processed (S109), then the available multi cap system (S110) may use a new cap for the next group to be cut (S114). Here it is also checked if all caps of the multi cap system are already full (S113), and if the answer is yes, the insertion of a new multi cap system is requested (S115).

Figure 4:
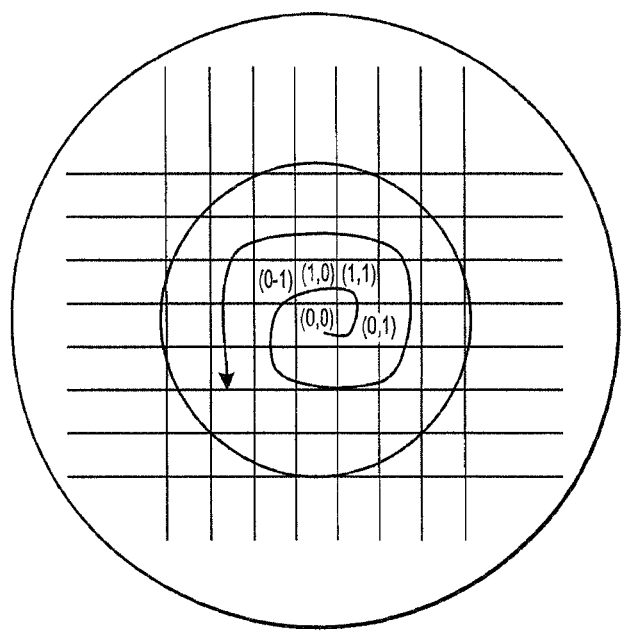
FIG. 4 shows a layout of a grid pattern subdividing the cap for accommodating the dissected specimen.

In the illustrated embodiment of the method, the positions (grid cells) are traversed by the slide along a spiral path. This is exemplified in FIG. 4. Here, the current cell indices Z=(Zx, Zy) are calculated to be

```
N = 0; Z = (0,0)
do N = N + 1
{       increase Zx by one until Zx = = N
        increase Zy by one until Zy = = N
        decrease Zx by one until Zx = = −N
        decrease Zy by one until Zy = = −N
}
D = (G · Zx, G · Zy).
```

From the examples illustrated herein, the skilled person will be able to recognize further advantageous embodiments, which also lie within the scope of this invention.

I claim:

1. A method for dissecting and collecting specimens, comprising:
   (a) placing a sample onto a slide of a laser dissection microscope, the slide being translatable in its plane of extension,
   (b) lowering an adherent collection device centered on the optical axis onto the sample, wherein the adherent collection device, in its lowered state, adheres to the sample, is freely translatable with the slide and decoupled from the optical axis of the microscope, and, in its raised state, is fixed relative to the optical axis,
   (c) dissecting one or more specimens from the sample, wherein each specimen is smaller than the entire sample, wherein the position of each specimen is input into a controller,
   (d) wherein the following steps are performed if the next specimen to be dissected is located outside of a predetermined collection radius of the adherent collection device:
      (i) raising the adherent collection device,
      (ii) translating the slide to a predetermined position relative to the optical axis of the microscope in order to decenter the center of the specimen to be dissected from the optical axis of the microscope,
      (iii) lowering the adherent collection device onto the sample, and
      (iv) dissecting one or more subsequent specimens,
   wherein, after each step of raising the adherent collection device, the predetermined position is spaced apart from all previously determined positions by at least one predetermined distance to allow collection of more than one specimen in a referenceable manner on a single adherent collection device,
   wherein prior to each dissection, the next specimen to be dissected is centered on the optical axis.

2. The method of claim 1, wherein the predetermined distance is defined by the maximum size of the specimens.

3. The method of claim 1, wherein the positions are located one after another along a spiral path.

4. The method of claim 1, wherein the adherent collection device, in its lowered state, lies flat on the sample.

5. The method of claim 1, wherein the adherent collection device, in its lowered state, lies on the sample with a controlled contact pressure.

6. The method of claim 1, wherein after the step of placing the sample onto the slide, the specimen(s) to be dissected is/are predetermined and, after any one step of raising the adherent collection device, the slide is translated relative to the adherent collection device so that the adherent collection device is located above a sample-free portion of the slide, followed by a step of determining the number and/or area of the dissected specimens and by a step of comparing the determined size and/or area with the number and/or area of the predetermined specimens before dissection.

7. The method of claim 6, wherein the step of predetermining comprises a step of setting a limit value for the difference in number and/or area between predetermined and determined numbers and/or areas of the specimens to be dissected.

8. The method of claim 6, wherein the step of comparing is performed by means of image analysis software.

9. The method of claim 6, wherein after the step of comparing, the adherent collection device is translated back above the sample in order to dissect specimens, that have not been dissected or adhered to the adhesive collection device properly, in accordance with the results of the comparison.

10. The method of claim 6, wherein after the step of comparing, a step of removing from the adherent collection device any undesired sample material by means of laser ablation is performed.

* * * * *